(12) United States Patent
Velazquez et al.

(10) Patent No.: US 11,464,816 B2
(45) Date of Patent: Oct. 11, 2022

(54) SUPPLEMENT FOR MENOPAUSE

(71) Applicant: The Procter & Gamble Company, Cincinnati, OH (US)

(72) Inventors: Jesus Velazquez, West Chester, OH (US); Leo Timothy Laughlin, II, Mason, OH (US); Brian Kenneth Burgdorf, Cincinnati, OH (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 220 days.

(21) Appl. No.: 17/079,551

(22) Filed: Oct. 26, 2020

(65) Prior Publication Data

US 2021/0038665 A1   Feb. 11, 2021

Related U.S. Application Data

(63) Continuation of application No. 16/384,920, filed on Apr. 16, 2019, now Pat. No. 10,849,948.

(51) Int. Cl.
| | |
|---|---|
| *A61K 36/15* | (2006.01) |
| *A61P 5/00* | (2006.01) |
| *A61K 36/81* | (2006.01) |
| *A61K 9/00* | (2006.01) |
| *A61K 45/06* | (2006.01) |
| *A23L 33/105* | (2016.01) |
| *A61K 31/522* | (2006.01) |

(52) U.S. Cl.
CPC ............ *A61K 36/15* (2013.01); *A23L 33/105* (2016.08); *A61K 9/0053* (2013.01); *A61K 31/522* (2013.01); *A61K 36/81* (2013.01); *A61K 45/06* (2013.01); *A61P 5/00* (2018.01); *A23V 2002/00* (2013.01)

(58) Field of Classification Search
None
See application file for complete search history.

(56) References Cited

U.S. PATENT DOCUMENTS

| | | | |
|---|---|---|---|
| 6,372,266 | B1 | 4/2002 | Suzuki |
| 6,506,419 | B2 | 1/2003 | Takahashi |
| 6,703,053 | B2 | 3/2004 | Tanaka |
| 6,926,914 | B2 | 8/2005 | Takahashi |
| 7,976,877 | B2 | 7/2011 | Willfoer |
| 8,017,147 | B2 | 9/2011 | Mazed |
| 8,303,995 | B1 | 11/2012 | Bryan |
| 8,337,909 | B2 | 12/2012 | Howard |
| 8,367,127 | B2 | 2/2013 | Moriguchi |
| 8,846,061 | B1 | 9/2014 | Bezzek |
| 8,962,038 | B2 | 2/2015 | Bryan |
| 9,119,823 | B2 | 9/2015 | Bryan |
| 9,308,230 | B2 | 4/2016 | Belcaro |
| 9,839,604 | B1 | 12/2017 | Tabibian |
| 2005/0276839 | A1 | 12/2005 | Rifkin |
| 2006/0292094 | A1 | 12/2006 | Bell |
| 2016/0038533 | A1 | 2/2016 | Bryan |
| 2016/0361353 | A1 | 12/2016 | Bryan |
| 2020/0330536 | A1 | 10/2020 | Velazquez |

FOREIGN PATENT DOCUMENTS

| | | | |
|---|---|---|---|
| WO | 9625939 | A1 | 8/1996 |
| WO | 2004089110 | A3 | 6/2005 |
| WO | 2007001506 | A1 | 1/2007 |
| WO | 2007006519 | A1 | 1/2007 |
| WO | 2009090085 | A8 | 8/2010 |
| WO | 2011041451 | A3 | 10/2011 |
| WO | 2011161655 | A1 | 12/2011 |
| WO | 2011018763 | A8 | 3/2012 |
| WO | 2017103946 | A3 | 7/2017 |
| WO | 2017153555 | A1 | 9/2017 |
| WO | 2017200391 | A1 | 11/2017 |
| WO | 2018017434 | A1 | 1/2018 |
| WO | 2018179011 | A1 | 10/2018 |

OTHER PUBLICATIONS

Donga Shilpa B; Dei Laxmipriya SO Ayu, (Oct. 2012) vol. 33, No. 4, pp. 511-516.*
All Office Actions, U.S. Appl. No. 16/384,920.
U.S. Appl. No. 16/384,920, filed Apr. 16, 2019, Velazquez, et al.

* cited by examiner

*Primary Examiner* — Michael V Meller
(74) *Attorney, Agent, or Firm* — Melissa G. Krasovec

(57) ABSTRACT

This disclosure relates to a supplement, particularly a supplement for menopause.

1 Claim, No Drawings

US 11,464,816 B2

SUPPLEMENT FOR MENOPAUSE

FIELD OF THE INVENTION

This disclosure relates to a supplement, particularly a supplement for menopause.

BACKGROUND OF THE INVENTION

Estimates indicate that by 2030 there will be about 1.2 billion menopausal and post-menopausal women in the world. Given that the average age at which menopause occurs has remained the same and that life expectancy among women has generally increased, the number of post-menopausal women is expected to grow. As such, there is increasing concern surrounding the conditions and symptoms experienced by perimenopausal, menopausal, post-menopausal women, and the need for treatment therefore is growing as well.

Menopause generally occurs 12 months after a woman's last menstrual period; however, it is considered a gradual process. Menopause is associated with a decrease in estrogen production and decreased estrogen levels may contribute to hot flashes, night sweats, mood changes, stress, fatigue, irritability, vaginal dryness, brain fog, and difficulty with memory. There are a variety of solutions that have been proposed to address the above-described symptoms. Prescription-based remedies have included hormone replacement therapy, which can include an estrogen supplement with or without progesterone. Hormone replacement therapy has also been reduced by contraindications such as a history of cancer and thromboembolism.

Different supplements, which contain botanical ingredients and other nutrients to help normalize hormone levels, are also available in the market today and vary in effectiveness. There is a need for a more effective remedy for the symptoms of menopause, a remedy which is non-hormonal and does not require a doctor's prescription. Women going through menopause experience high levels of oxidative stress and addressing this oxidative stress may help manage menopause symptoms. Surprisingly, it has been found that certain combinations of pine bark and ashwagandha, at select ratios, provide a synergistic antioxidant effect that helps improve symptoms of menopause.

SUMMARY OF THE INVENTION

A supplement composition comprising ashwagandha extract and a pine bark extract, where the weight ratio of ashwagandha extract to the pine bark extract is about 1:5 to about 25:1 and where the supplement composition is formulated to treat the symptoms of menopause.

A supplement composition comprising a daily intake comprising from about 50 mg to about 1250 mg ashwagandha extract and from about 10 mg to about 300 mg of a French maritime pine bark extract, where the weight ratio of ashwagandha extract to French maritime pine bark extract is about 1:5 to about 25:1 and where the supplement composition is formulated to treat the symptoms of menopause.

A method of treating a symptom of menopause in a woman, the method comprising the steps of:
  a. providing a supplement composition comprising ashwagandha extract and a pine bark extract, where the weight ratio of ashwagandha extract to pine bark extract is about 1:5 to about 25:1;
  b. orally administering the supplement composition to a woman in need thereof.

DETAILED DESCRIPTION

While the specification concludes with claims particularly pointing out and distinctly claiming the subject matter of the present invention, it is believed that the invention can be more readily understood from the following description.

Various non-limiting embodiments of the present disclosure will now be described to provide an overall understanding of the principles of the compositions and methods disclosed herein. Those of ordinary skill in the art will understand that the embodiments and methods described herein are non-limiting example embodiments and that the scope of the present disclosure is defined solely by the claims. The features illustrated or described in connection with one non-limiting embodiment can be combined with the features of other non-limiting embodiments. Such modifications and variations are intended to be included within the scope of the present disclosure.

All percentages are by weight of the supplement composition, unless specifically stated otherwise. All ratios are weight ratios, unless specifically stated otherwise. All ranges are inclusive of narrower ranges and combinable. Delineated upper and lower range limits are interchangeable to create further ranges not explicitly delineated. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity.

The compositions of the disclosure can comprise, consist essentially of, or consist of, the components as well as optional ingredients described herein. As used herein, "consisting essentially of means that the composition or component may include additional ingredients or features, but only if the additional ingredients or features do not materially alter the basic and novel characteristics of the claimed compositions or methods. As used in the description and the appended claims, the singular forms "a," "an," and "the" are intended to include the plural forms as well, unless the context clearly indicates otherwise. Unless otherwise defined, all technical and scientific terms used herein have the same meaning as commonly understood by one of ordinary skill in the art to which this invention belongs.

As used herein, the terms "administer," "administering," and "administration," refer to any method which, in sound medical practice, delivers the supplement to a subject in such a manner as to provide a therapeutic effect.

As used herein, the term "non-GMO" means that the product has been verified as fully compliant to the Non-GMO Project Standard. Meets the standards of the non-GMO Project Standard as of May 21, 2014, and thus the product can be labeled Non-GMO Project Verified.

As used herein, the term "organic" means that the ingredient complies with International Certification Services, Inc. (ICS) organic guidelines (available Sep. 12, 2016) which states that the ingredient needs to be at least 70% organic.

As used herein, the term "supplement" refers to a supplement intended to supplement a diet of food and water, where the diet is sufficient to support life. A supplement may contain vitamins, minerals, herbs or other botanicals, amino acids, enzymes, organ tissues, glandular metabolites, actives for energy support, actives for sleep support, or combinations thereof. The botanical can be from culture media. A supplement may be an extract or concentrate of a particular food source or a particular nutrient. Supplements may be administered by any convenient means, including parenteral or enteral routes. Enteral routes may include oral, gastric, or subgastric administration, including rectal administration.

As used herein, the term "vegetarian" refers to a product, including but not limited to foods and supplements, which are not made from or with the aid of products derived from animals that have died, have been slaughtered, or animals that die as a result of being eaten. Animals means farmed, wild or domestic animals, including, but not limited to, livestock poultry, game, fish, shellfish, crustacea, amphibians, tunicates, echinoderms, mollusks and insects. In one example, a product can be vegetarian if it includes dairy products and eggs.

As used herein, the term "vegan" refers to a product including, but not limited to foods and supplements, which are not made from or with the aid of animals or animal products (including products from living animals).

"Estrogen agent" means any natural or synthetic estrogen hormone (e.g., estrone, estradiol and estriol), metabolites thereof, esters thereof, analogues thereof, phytoestrogens (e.g., isoflavones, coumestans, prenylflavonoids), estrogen precursors (e.g., dehydroepiandrosterone) and/or any compound which binds to an estrogen receptor or which otherwise exhibits at least mild or weak estrogen-like effects, including selective estrogen receptor modulators ("SERM") such as, for example: afimoxifene (4-hydroxytamoxifen), arzoxifene, bazedoxifene, clomifene, femarelle (DT56a), lasofoxifene, ormeloxifene, raloxifene, tamoxifen, toremifene, mifepristone (RU486), VA2914, ulipristal, Proellex, Asoprisnil, and CDB-4124.

Menopause, in the absence of hormone replacement therapy or other medication, is a gradual process that a woman experiences and may comprise three stages: perimenopause stage or menopause transition, menopause stage, and postmenopause stage. As used herein, the term "menopause" is understood to mean one or more of these three stages. The menopause stage is the point when a woman no longer has menstrual periods. At this stage, the ovaries have stopped releasing eggs and producing most of their estrogen. The menopause stage is diagnosed when a woman has gone without a period for 12 consecutive months.

A "perimenopausal" woman is one who in the absence of hormone replacement therapy or other medication would experience a change in her intermenstrual cycle interval and have associated symptoms of estrogen deficiency, such as vasomotor flushes, vaginal dryness and/or worsening premenstrual syndrome. Also included are women who in the absence of hormone replacement therapy or other medication would experience less than 12 months amenorrhea. Perimenopause may begin eight to ten years before menopause, when the ovaries gradually produce less estrogen. Perimenopause lasts up until menopause, the point when the ovaries stop releasing eggs. In the last one to two years of perimenopause, the drop in estrogen accelerates. At this stage, many women can experience menopause symptoms.

"Pharmacologically effective amount", "therapeutically effective amount" or simply "effective amount" means the amount of a composition, or ingredient thereof, effective to produce the intended pharmacological, therapeutic or preventive result.

The "postmenopause" stage comprises the years after menopause. During this stage, a woman, in the absence of hormone replacement therapy or other medication, may still experience menopausal symptoms, such as hot flashes, but these symptoms may ease.

"Progesterone agent" means any natural or synthetic progesterone hormone, metabolites thereof, analogues thereof, progesterone precursors and/or any compound which binds to a progesterone receptor or which otherwise exhibits at least mild or weak progesterone-like effects, including selective progesterone receptor modulators ("SPRM") such as, for example, telapristone.

"Substantially free" means a component or material is present in amount less than 0.1%, 0.05%, 0.025%, 0.01%, or 0.001% by weight of the vaginal care composition.

"Vaginal care composition" means any composition that is suitable for application to the vaginal introitus and/or one or more of the vulva, vestibule, labia majora, labia minora, and/or external urogenital tract and which is useful for treating or ameliorating vaginal dryness.

Menopause, when it occurs between the ages of 45 and 55, is considered "natural" and is a normal part of aging. Some women may experience menopause early, either as a result of a surgical intervention (such as removal of the ovaries) or damage to the ovaries (such as from chemotherapy). Menopause that occurs before the age of forty five, regardless of the cause, is called early menopause. Menopause that occurs at 40 or younger is considered premature menopause. Regardless of when menopause begins, it may be accompanied by a number of symptoms, including hot flashes (a sudden feeling of warmth that spreads over the body), night sweats and/or cold flashes, vaginal dryness (which may contribute to discomfort during sex), urinary urgency (a pressing need to urinate more frequently), difficulty sleeping (insomnia), emotional changes (irritability, mood swings, mild depression), dry skin, dry eyes, or dry mouth.

Women who are still in the menopause transition (perimenopause) may also experience breast tenderness, worsening of premenstrual syndrome (PMS), irregular periods or skipping periods, periods that are heavier or lighter than usual. Some women may also experience a racing heart, headaches, joint and muscle aches and pains, changes in libido (sex drive), difficulty concentrating, memory lapses (often temporary), weight gain, and hair loss or thinning. These symptoms may be a sign that the ovaries are producing less estrogen.

Because the symptoms of menopause may be quite disruptive, some woman may desire a treatment to help manage or treat the symptoms of menopause, preferably an easy-to-use treatment that facilitates compliance. Some women may desire a supplement to help manage or treat the symptoms of menopause. In particular, some women may be looking for a supplement that can reduce hot flashes, night sweats and/or cold flashes, vaginal dryness, difficulty sleeping (insomnia), emotional changes (irritability, mood swings, mild depression), and other symptoms of menopause. This can be achieved by selecting ingredients, in particular herbal ingredients, that can target multiple biological pathways, including reducing oxidative stress. In some examples, the supplement can be a non-GMO supplement that can contain organic ingredients.

The supplement composition may comprise a daily intake comprising from about 50 mg to about 1250 mg, or from about 60 mg to about 1000 mg, or from about 75 mg to about 500 mg, or from about 100 mg to about 250 mg of ashwagandha extract and from about 10 mg to about 300 mg, or from about 20 mg to about 250 mg, or from about 30 mg to about 225 mg, or from about 40 mg to about 200 mg, or from about 50 mg to about 150 mg of the pine bark extract.

Pine Bark

The pine bark may comprise an extract from a French maritime pine bark, for example, a pine bark extract commercially available as Pycnogenol® (Horphag), which is a pine bark extract of the French maritime pine *Pinus pinaster*, Aiton, subspecies *Atlantica* des Villar, standardized to contain from about 65% to about 75% of proanthocyanidins).

*Pinus pinaster* (*P. pinaster*) and *Pinus maritima* (*P. maritime*), are understood to refer to the same organism commonly called "French Maritime Pine." Hence, these terms are interchangeable.

The pine bark extract may contain proanthocyanidins, which may work as antioxidants. Proanthocyanidins designates a group of flavonoids that includes the subgroups procyanidins, prodelphinidins and propelargonidins. Proanthocyanidins are homogeneous or heterogeneous polymers consisting of the monomer units catechin or epicatechin, which are connected either by 4-8 or 4-6 linkages, to the effect that a great number of isomer proanthocyanidins exist. Typically, the proanthocyanidins oligomers have a chain length of 2-12 monomer units. Preferably, the pine bark extract contains procyanidins. The pine bark extract may contain at least about 40% procyanidin by weight of the pine bark extract, or from about 50% procyanidin by weight of the pine bark extract to about 100% procyanidin by weight of the pine bark extract.

The supplement composition may contain other pine bark extract(s), including extracts of *Pinus radiata* (New Zealand pine), *Pinus sylvestris* (Scots pine), *Pinus pinaster* Sol. in Ait., *Pinus radiata, Pinus koraiensis, Pinus pumila, Pimus luchuensis, Pinus palustris, Pinus bungeana, Pinus thunbergii, Pinus densiflora, Pinus parviflora, Pinus pentaphylla, Pinus koraiensis, Pinus pumila, Pimus luchuensis, Pinus tabulaeformis, Pinus palustris* or *Pinus bungeana* or a mixture of these.

The supplement composition may contain from about 10 mg to about 300 mg, or from about 20 mg to about 250 mg, or from about 30 mg to about 225 mg, or from about 40 mg to about 200 mg, or from about 50 mg to about 150 mg of pine bark extract per daily intake.

Ashwagandha

Ashwagandha, also known as *Withania somnifera*, Indian ginseng, and winter cherry, is a plant in the Solanaceae or nightshade family. It has been an important herb in the ayurvedic and indigenous medical system for over 3000 years. Ashwagandha grows as an erect, greyish, subshrub with inconspicuous yellow or greenish flowers followed by small, spherical, orangish-red berries containing yellow, kidney-shaped seeds. It grows three-to-five feet tall, mainly in drier regions, and is cultivated widely as the whole plant; most commonly the root and leaf are used medicinally. The fruits from several of its species are edible, and some are used in traditional medicine.

The supplement composition may contain an Ashwagandha extract prepared from only the leaves, only the root, or from the whole plant, using conventional methods of extraction. The supplement composition may contain from about 50 mg to about 1250 mg, or from about 60 mg to about 1000 mg, or from about 75 mg to about 500 mg, or from about 100 mg to about 250 mg of ashwagandha extract, per daily intake.

Ratio of Ashwagandha to Pine Bark

Menopause is associated with a decrease in estrogen production and decreased estrogen levels and estrogen is a known antioxidant. The decrease in estrogen levels may contribute to oxidative stress in various tissues, due to the release of reactive oxygen species, which in turn may contribute to a variety of symptoms of menopause.

The supplement compositions may contain ashwagandha and pine bark in a weight ratio of about 1:1 to about 25:1, or about 1:1 to about 20:1, or about 5:1 to about 10:1. It has surprisingly been found that certain weight ratios of ashwagandha to pine bark provide synergistic antioxidant activity, as measured by the Nrf2 transcription factor assay. The antioxidant benefits may take longer to take effect. The user may need to take the supplement composition daily for two, four, six, eight, or twelve weeks before antioxidant benefits are realized.

Additional Actives

The supplement can further contain one or more additional actives, preferably an active for energy support or an active for sleep support. An active for energy support or an active for sleep support may provide an acute benefit, for example, within about ten, or about fifteen, or about thirty, or about sixty minutes of ingestion. The addition of an active for energy support or an active for sleep support may help promote compliance and encourage long term adoption. For example, a user may be more likely to adopt the habit of ingesting the composition in the evening, if it helps them fall asleep or stay asleep. Or, the user may be more likely to adopt the habit of ingesting the composition in the morning, if it helps them wake up or be more alert.

The active for energy support may comprise caffeine or other xanthine compounds, such as xanthine, i-methyl xanthine, theophylline, theobromine, derivatives thereof, and/or mixtures thereof. Among these compounds, caffeine is preferred. The active for energy support may be derived from tea, such as green tea, white tea, black tea, or oolong tea, yerba mate, coffee, guarana, derivatives thereof, and/or extracts thereof. Thus, the source of the active for energy support may be a natural extract. Alternatively, the active for energy support may be synthetic. Caffeine and other xanthine compounds may act as stimulants and improve reaction time, wakefulness, concentration, and motor coordination, while reducing fatigue and drowsiness. Caffeine may be beneficial to users suffering from menopause symptoms, such as fatigue and brain fog. However, caffeine may be metabolized differently in different people and, in some people, increased levels of caffeine may worsen symptoms. The supplement composition may comprise up to about 75 mg of caffeine, or from about 1 mg to about 50 mg of caffeine, or from about 25 mg to about 50 mg of caffeine.

The active for sleep support may comprise or be derived from chamomile, melatonin, valerian, passion flower, hops, Kava, magnesium, lavender, glycine, tryptophan, L-Theanine, *Ginkgo biloba*, or combinations thereof. Generally, a supplement containing an active for sleep support is substantially free of an active for energy support and a supplement containing an active for energy support is substantially free of an active for sleep support. The supplement composition may comprise from about 0.1 mg to about 15 mg, or about 0.3 mg to about 12 mg, or about 0.5 mg to about 10 mg, or about 1 mg to about 8 mg of melatonin. The supplement composition may comprise from about 50 mg to about 1200 mg, or about 100 mg to about 1000 mg, or about 300 mg to about 900 mg, or about 400 mg to about 800 mg of valerian. The supplement composition may comprise from about 50 mg to about 1200 mg, or about 100 mg to about 1000 mg, or about 300 mg to about 900 mg, or about 400 mg to about 800 mg of passion flower. Dosing for other sleep support actives, such as chamomile, hops, Kava, magnesium, lavender, glycine, tryptophan, L-Theanine, and

*Ginkgo biloba* can be found in Botanical Medicines: The Desk Reference for Major Herbal Supplements, Second Edition, Mckenna et al., Routledge, Nov. 12, 2012, which is hereby incorporated by reference.

Form

In a preferred form, the supplements of the present invention are administered orally. Oral administration dosage forms include, without limitation, tablets, capsules, softgels, gelcaps, gummies, liquids, powders, and films, as well as food-like forms such as bars, candies, lozenges, beverages, and the like. The supplement composition may be a capsule. The supplement composition may be a two-piece capsule. The supplement composition may be vegetarian.

The supplement composition can also contain flow agents. Non-limiting examples of flow agents can include rice, rice hull extract, gum acacia, silica, lac resin, carnauba wax, maltodextrin, and combinations thereof. The gum acacia or rice can be organic.

The dosage form may be a capsule. Each capsule can contain from about 100 mg of ingredients to about 1000 mg, in another example from about 200 mg to about 735 mg, in another example from about 250 mg to about 500 mg, and in another example from about 300 mg to about 400 mg. The capsule shell can be one-piece or two-pieces. The capsule shell can contain one or more polymers, where the polymers can be vegetarian and/or non-GMO. The capsule shell can contain a polymer selected from the group consisting of hydroxypropyl methylcellulose, pullulan, and combinations thereof. The capsule shell can be substantially free of gelatin. The capsule shell can be substantially free of gelling agents and/or other ingredients. The capsule shell can also contain coloring agents, preservatives, disintegrants, lubricants and surface treatments.

Method of Use

The supplement composition can be administered as the only dietary supplement. The supplement composition can be administered with additional dietary supplements, such as fish oil, a multivitamin, a supplement composition to support the body's healthy inflammation response, a supplement composition that supports cardio, a supplement composition that supports intestinal health. The additional supplement composition can be a turmeric supplement and/or a ginger supplement.

The supplement composition can be taken once daily. Alternatively, the supplement can be taken twice daily, or three times daily, or four times daily, and or more than four times daily. The supplement composition can be taken with meals. The supplement composition can be taken in the morning, mid-day, afternoon, evening, and/or night, depending on whether the supplement contains actives for sleep support, actives for energy support, or no additional actives. The supplement composition can be taken at the same time every day or the time the supplement composition is taken can vary. The daily intake can be contained in a single dosage that can be consumed once daily, or the daily intake can be contained in multiple dosages that can be taken either together or separately throughout the day.

The supplement can contain potent antioxidant action from the combination of pine bark extract, such as the pine bark extract sold commercially as Pycnogenol®, and ashwagandha. Procyanadins in the pine bark extract in combination with ashwagandha can provide potent antioxidant activity. The supplement can treat symptoms of menopause. The supplement can treat hot flashes, night sweats, mood changes, stress, fatigue, irritability, vaginal dryness, brain fog, difficulty with memory, or a combination thereof.

The supplement can be gluten free, vegetarian, non-GMO, dairy free, free of eggs and egg products, kosher certified, halal certified, or a combination thereof. The supplement may be substantially free of gelatin. All or some of the supplement ingredients can be organic.

The supplement may be used in combination with a treatment for vaginal dryness. The treatment for vaginal dryness may comprise applying a vaginal moisturizer to the vagina or parts of the vagina. The treatment for vaginal dryness may also comprise an applicator for applying the vaginal moisturizer. The applicator, vaginal moisturizer, and supplement may be sold in a kit and used as part of a regimen.

EXAMPLES

Example 1

This example demonstrates the ability of an effective amount of ashwagandha and pine bark, in the selected weight ratios, to synergistically activate the Antioxidant Response Element (ARE). A general schematic for how the ARE reporter assay operates to identify agents that promote transcription of the ARE is described in U.S. Publication No. 2011/0262570.

ARE activation was quantitated using the ARE-32 reporter cell line available from CXR-Biosciences as described in the ARE Assay below. ARE32 is a stable MCF7 cell line containing pGL8x-ARE (8 copies of the rat GST ARE linked to the luciferase gene) and pCDNA3.1, which contains the neomycin selectable marker. Selection was performed in the presence of G418 and resistant clones were isolated. Clones were screened for induction of luciferase in response to tBHQ (tert-Butylhydroquinone). Reagents and Instruments used in this example are provided below. It is to be appreciated that equivalent reagents and instruments may be substituted for those shown, as long as the substitution does not alter the results of the assay.

Summary of Method

The assays are performed using expanded and cryopreserved passaged stocks from the liquid nitrogen storage. The cells are first expanded over 4-5 days in culture flasks and passaged every 3-4 days (when cells are ~80% confluent). When cells are >70% confluent or ready to seed into 96 well plates the cells are trypsinized, seeded and grown in 96-well plates. After growing for 1 days in 96-well plates, media is replaced with fresh treatment media (phenol red free, no FBS) and cells are treated with compounds and incubated overnight (24 hours). Post treatment, cells are rinsed with 1×PBS, lysed and receive the luciferase kit reagent and luminescence measured.

Equipment

Biological Safety Cabinet
Multi-channel pipette
Inverted Microscope
Water Bath
Bench top centrifuge
Incubator
Plate Reader (that can read luminescence)
Corning 3275 cell culture flask (or comparable)
Pipets and pipette controller (ex/Pipet Boy, Drummond Pipet)
Aspirator that uses pipet tips and hooks to house vacuum
96-well plate (Costar, Cat #3903 or 3610)

Cells and Cell Reagents

Dulbecco's Modified Eagle Medium (DMEM) (Gibco™, Cat #11054-020)

Fetal Bovine Serum Heat Inactivated (FBS) (Gibco™, Cat #A31604)

Geneticin G418 sulphate (G418) (Gibco™, Cat #10131-027)

Penicillin-Streptomycin 100× (Gibco™, Cat #15140-148)

GlutaMAX Supplement 100× (Gibco™ 35050-061)

0.25% Trypsin EDTA (Gibco™ 25200-056)

0.4% Trypan Blue if using hemocytometer to count cells

1×PBS

Maintenance and Plating Media 500 ml DMEM (Gibco, Cat #11054-020)

0.8 mg/ml G418

5 ml GlutaMAX 50 ml FBS 5 ml Pen/Step.

Treatment media (treatment media is the same media without the addition of G418 or FBS).

500 ml DMEM (Gibco, Cat #11054-020)

5 ml GlutaMAX 5 ml Pen/Step.

Starting New Cultures

AREC32 cells are from CXR BioSciences. Cells are frozen in medium contains 90% FBS and 10% DMSO and stored in liquid nitrogen. When starting a new culture of cells thaw vial from liquid nitrogen quickly and add to 50 ml conical tube with 25 ml media. Centrifuge at 1500-2000 RPM for 5 minutes. Remove media without disturbing cell pellet. Re-suspend cells in 12 ml media and add to T-75 tissue culture flask. Cells should be at >80% confluency in 4-5 days and can be split 1:3 into T-150 flasks to grow cells for seeding plates if more cells are needed.

Maintaining and Sub-Culturing Cells:

Cells are maintained and plated in DMEM 11054-020 with the added components above Subculture (passage cells) every 3-4 days or when ~75-80% confluent. To passage cells, aspirate media from flask and add 6 ml 0.25% trypsin. Tilt flask in all directions to distribute the trypsin over the bottom of the flask and place in incubator. After 2-3 minutes observe cells under microscope to see if detached. If cells have not detached completely place in incubator for an additional 2-3 minutes. Once detached add 6 ml DMEM maintenance media to neutralize trypsin and pipet into centrifuge tube. Centrifuge at 1200 RPM for 5 minutes. Remove media without disturbing cell pellet. Re-suspend pellet in 12 ml DMEM maintenance/plating media and add to flask. If splitting or detaching cells from a T-150 flask double all volumes and follow same procedures.

Plating Cells

Aspirate media from flask and add appropriate volume of 0.25% trypsin depending on size of flask (6 ml for T-75 and 12 ml for T-150 flask). Swirl flask to distribute trypsin on bottom of flask and return to incubator for 2-3 minutes. Observe cells under microscope. If cells have not detached completely place in incubator for an additional 2-3 minutes. Once cells are detached add maintenance DMEM equal to the volume of trypsin, mix gently and place in centrifuge tube. Centrifuge at 12000 RPM for 5 minutes. Aspirate media without disturbing cell pellet. Re-suspend pellet in 10 ml DMEM. Dilute the cells 1:5 using 50 µl cells+200 µl DMEM. Use 20 µl of this dilution and 20 µl 0.4% trypan blue. Mix and add 10 µl/chamber to disposable hemocytometer. Non-viable cells will be blue, viable cells will be unstained. Count cells under the microscope in four 1×1 mm squares of one chamber and determine the average number of cells per square (all hemocytometers consist of two chambers; each is divided into nine 1 mm2 squares). For an accurate determination, the total number of cells overlying one 1 mm2 should be between 20-50 cells/square. If the cell density is higher than 200 cells/square, you should dilute your cell suspension. Count cells on disposable hemocytometer. Calculate #cells/ml. Cells may be counted either with a hemocytometer or by using an automatic counter such as Countess FII (Life technologies). It is recommended cells be >90% viable for seeding/assaying. Cell seeding density may vary from ~10,000 cells/well or more depending on how well the passage of cells grows. Cell density should be ~70-80% on day of treatment/dosing.

On day 2 when test materials are added media is replaced with the DMEM treatment media (Gibco Cat #11054-020. Do not add FBS, Glutamax or Pen-Strep. This media is phenol red free and will be clear. Phenol red can react with the luciferase assay reagents.

Positive Control: Tert-Butylhydroquinone (tBHQ) (Aldrich, Cat #11,294-1). Prepare 100 mM stock. MW=166.21. 1M=166.21 g/L or mg/ml. 100 mM=16.62 mg/ml. Prepare 10 ml using 166.62 mg or 0.166 g. Dilute to 750 µM or 1:133 using 30 µl of 100 mM tBHQ+3.62 ml treatment media. When 41 is added to the assay well containing 200 µl the f.c. is 7.5 µM.

Test Materials

Test materials will be prepared in DMSO or water. The final concentration of DMSO should never exceed 1%.

Procedure—Cell Preparation and Treatment

In a 96 well-plate, seed $1.5 \times 10^4$ cells/well* in 100 µl DMEM maintenance/plating media. Let cells sit for 15 minutes at room temp. post seeding prior to placing in incubator to allow the cells to settle. Incubate the cells at 37° C. in a 5% $CO_2$, 95% humidity incubator for 24 hrs. Replace the medium with 99 µl DMEM treatment media and treat with test compounds 2 µl per well, vehicle 2 ul/well and positive control tBHQ 2 µl/well (f.c. 7.5 µM). Add 99 µl of media after treatment, final assay volume 200 µl: Adding half the media after dosing insures better distribution of the materials. Incubate the cells at 37° C. in $CO_2$, 95% humidity incubator for another 24 hrs. Remove media and wash the cells once with 100 µl 1×PBS buffer. Remove PBS and follow instructions for luciferase assay.

Luciferase Assay

Luciferase Reagents: Luciferase Assay System including lysis buffer (Promega, Cat #E4530). Prepare 1× lysis reagent by adding 4 volumes of water to 1 volume of 5× lysis reagent. Add 20 µl of lysis buffer per well. Gently shake plate to distribute buffer in well. Place plate in −80° C. freezer for 15 minutes to facilitate lysis. Thaw plate completely. Confirm lysis under microscope. Prepare Luciferase Assay Reagent (LAR) by adding Luciferase Assay Buffer (10 ml for E152A and 100 ml for E152B) to the vial of lyophilized Luciferase Assay Substrate. Mix gently. Add 100 µl Luciferase Assay Reagent per well. Ensure there are no air bubbles. Read plate immediately using Neo2 plate reader.

All assay legs were run with n=3. Ashwagandha and Pycnogenol tested levels are as indicated in the data tables and reflect actual levels in the well.

As shown in Table 1, all of the weight ratios of ashwagandha to pine bark activate nrf-2. Certain weight ratios of ashwagandha to pine bark, however, show synergistic activation. In Table 1, synergy factors of greater than about 1.3 indicate synergistic antioxidant activity. An example calculation of a synergy factor is shown in Table 2. Table 1 shows that ashwagandha to pine bark weight ratios of 1:1, 5:1, 10:1, 20:1, and 25:1 provide a synergistic effect.

TABLE 1

Test for synergy in ARE nrf-2 for binary combinations of ashwagandha and pine bark

| Sample | Ashwagandha[1] (w/v %) | Pine bark[2] (w/v %) | Ashwagandha: pine bark | ARE nrf-2 | Synergy Factor |
|---|---|---|---|---|---|
| 1 | 0.001% | 0.01% | 1:10 | 13 | 0.8 |
| 2 | 0.001% | 0.005% | 1:5 | 22 | 1.7 |
| 3 | 0.001% | 0.001% | 1:1 | 53 | 3.6 |
| 4 | 0.001% | 0.0002% | 5:1 | 74 | 8.7 |
| 5 | 0.001% | 0.0001% | 10:1 | 68 | 6.3 |
| 6 | 0.001% | 0.00005% | 20:1 | 39 | 4.2 |
| 7 | 0.001% | 0.00004% | 25:1 | 18 | 2.3 |
| 8 | 0.001% | 0.00002% | 50:1 | 11 | 1.1 |

[1]Sensoril ®, an extract using the whole ashwagandha plant, is commercially available from Natreon 14 Home News Row, New Brunswick, NJ 08901 USA.
[2]Pycnogenol ®, commercially available from Horphag Research Avenue Louis-Casaï 71 CH-1216 Cointrin Geneva, Switzerland.

TABLE 2

Example of Activation Data and Synergy Factor Calculations (A = ashwaganda, PB = pine bark)

| | Vehicle control Observed | 0.001% A (root, leave) Observed | 0.001% PB Observed | 0.001% A + 0.001% PB Observed | 0.001% A + 0.001% PB Expected | Synergy Factor (observed combination/expected combination) |
|---|---|---|---|---|---|---|
| Luminescence | 636 | 8014 | 5043 | 49613 | 13057 | 49613/13057 = 3.8 |
| Fold over control | 1.00 | 8014/636 = 12.6 | 5043/636 = 7.9 | 78 | 20.5 | 78/20.5 = 3.8 |

Example 2

A consumer test is run with consumers who are experiencing symptoms of menopause. The supplement composition contains 100 mg of Pycnogenol and 125 mg of ashwagandha, as the active ingredients. Each participant is instructed to ingest one supplement daily for a period of 12 weeks. Each participant is asked to rate her overall experience with the supplement in regard to addressing her menopause symptoms on a scale of 1 to 5—with a rating of one being worst and a rating of five being best—after 4, 8, and 12 weeks of usage. The number of participants who responded to the request for a rating and the average rating of all consumers is presented in Table 3. It is observed that the supplement rating increased from 3.3 at 4 weeks to 3.8 after 12 weeks, which is statistically significant with 95% confidence. This suggests the supplement effectiveness improves over time.

TABLE 3

Average Consumer Ratings

| Number of weeks | 4 | 8 | 12 |
|---|---|---|---|
| Number of People Responded | 42 | 42 | 42 |
| Average Product Rating (1-5) | 3.3 | 3.6 | 3.8 |

TABLE 4

Menopause Symptoms Improve

| | | Pycnogenol & Ashwagandha | | |
|---|---|---|---|---|
| | Week | 4 | 8 | 12 |
| Hot Flashes Better | base[1] | 39 | 40 | 39 |
| | | 67% | 66% | 77% |
| Night Sweats Better | Base | 39 | 40 | 38 |
| | | 68% | 65% | 77% |
| Mood Swings Better | Base | 35 | 31 | 34 |
| | | 56% | 64% | 70% |
| Brain Fog Better | Base | 39 | 34 | 37 |
| | | 56% | 63% | 70% |
| Stress Better | Base | 39 | 37 | 35 |
| | | 36% | 55% | 55% |
| Disrupted Sleep Better | Base | 41 | 40 | 40 |
| | | 54% | 61% | 62% |

[1]Some of the 42 participants did not report having these symptoms, hence the difference in base size.

Example 3: Supplement Compositions

TABLE 5

| | Formulas | | | | |
|---|---|---|---|---|---|
| Ingredient | Total input qty per Capsule in mg. | | | | |
| SENSORIL@(STD, EXT OF ASHWAGANDHA ROOT& LEAF) Powder | 125 | 500 | 500 | 250 | 500 |
| PYCNOGENOL | 100 | 200 | 100 | 60 | 100 |
| FLOW AGENT | 40.00 | 42.00 | 43.00 | 39.00 | 40.00 |
| CAPSULES -SIZE 1 WHITE VEGGIE CAPSULES KOSHER | 72.00 | 72.00 | 72.00 | 72.00 | 72.00 |
| MELATONIN (MIN, 98.5%) | 2.00 | 2.00 | 4.00 | 0.00 | 0.00 |
| GREEN TEA EXTRACT (25 mg caffeine) | 0.00 | 0.00 | 0.00 | 100 mg | 0.00 |

Values disclosed herein as ends of ranges are not to be understood as being strictly limited to the exact numerical values recited. Instead, unless otherwise specified, each numerical range is intended to mean both the recited values and any real numbers including integers within the range. For example, a range disclosed as "1 to 10" is intended to mean "1, 2, 3, 4, 5, 6, 7, 8, 9, and 10" and a range disclosed as "1 to 2" is intended to mean "1.1, 1.2, 1.3, 1.4, 1.5, 1.6, 1.7, 1.8, 1.9, and 2."

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating menopause in a woman in need thereof consisting essentially of orally administering to the woman in need thereof therapeutically effective amounts of an ashwagandha extract and pine bark extract to effectively treat the menopause in the woman in need thereof wherein the ratio of the ashwagandha extract to the pine bark extract is 5:1 to about 10:1, respectively.

* * * * *